(12) United States Patent
Andersen et al.

(10) Patent No.: US 7,799,776 B2
(45) Date of Patent: Sep. 21, 2010

(54) INDOLEAMINE 2,3-DIOXYGENASE (IDO) INHIBITORS

(75) Inventors: Raymond J. Andersen, Vancouver (CA); Alban Pereira, Vancouver (CA); Xin-Hui Huang, Vancouver (CA); Grant Mauk, Vancouver (CA); Eduardo Vottero, Vancouver (CA); Michel Roberge, Vancouver (CA); Aruna Balgi, Vancouver (CA)

(73) Assignee: The University of British Columbia, Vancouver, British Columbia (CA)

( * ) Notice: Subject to any disclaimer, the term of this patent is extended or adjusted under 35 U.S.C. 154(b) by 579 days.

(21) Appl. No.: 11/632,629

(22) PCT Filed: Jul. 13, 2005

(86) PCT No.: PCT/CA2005/001087

§ 371 (c)(1),
(2), (4) Date: Dec. 19, 2007

(87) PCT Pub. No.: WO2006/005185

PCT Pub. Date: Jan. 19, 2006

(65) Prior Publication Data

US 2009/0042868 A1    Feb. 12, 2009

Related U.S. Application Data

(60) Provisional application No. 60/587,060, filed on Jul. 13, 2004.

(51) Int. Cl.
C07D 513/04    (2006.01)
C07D 279/14    (2006.01)
A61K 31/5415   (2006.01)

(52) U.S. Cl. .................................. 514/222.8; 544/32
(58) Field of Classification Search .................. 544/32; 514/222.8
See application file for complete search history.

(56) References Cited

U.S. PATENT DOCUMENTS

| | | | |
|---|---|---|---|
| 4,771,036 | A | 9/1988 | Pigiet et al. |
| 6,451,840 | B1 | 9/2002 | Munn et al. |
| 6,482,416 | B2 | 11/2002 | Munn et al. |
| 6,500,813 | B1 | 12/2002 | Itoh et al. |
| 2004/0234623 | A1 | 11/2004 | Munn et al. |

FOREIGN PATENT DOCUMENTS

| | | |
|---|---|---|
| WO | WO 2004/093871 A1 | 11/2004 |
| WO | WO 2004/094409 A1 | 11/2004 |

OTHER PUBLICATIONS

Harada, Nobuyuki et al., *Synthesis and Absolute Stereochemistry of (+)-Adociaquinones A and B*, Tetrahedron: Asymmetry, vol. 6, pp. 375-376 (1995).

Aiello, Anna et al., *Conicaquinones A and B, Two Novel Cytotoxic Terpene Quinones from the Mediterranean Ascidian Aplidium conicum*, Eur. J. Org. Chem., 2003, pp. 898-900.

Fahy, Eoin et al., *Annulins A and B, Metabolites of the Marine Hydroid Garveia annulat*, J. Org. Chem. 1986, 51, 5145-5148.

Fahy, Eoin et al., *Metabolites of the Marine Hydroid Garveia annulata: Garveatins B and C, 2-Hydroxygarvin, and Garvin A Quinone*, J. Org. Chem., 51, 57-61 (1986).

Schmitz, Francis. J., et al., *Xesto- and Halenaquinone Derivatives from a Sponge, Adocia sp., from Truk Lagoon*, J. Org. Chem., 1988, 53, 3922-3925.

Fahy, Eoin et al., *Minor metabolites of the marine hydroid Garveia-annulata*, Can J. Chem. vol. 65, 1987 pp. 376-383.

Concepcion, G.P., et al., *Topoisomerase II-Mediated DNA Cleavage by Adocia- and Xestoquinones from the Phillippine Sponge Xestospongia sp.*, J. Med. Chem., 1995, 38, 4503-4507.

Cao, Shugeng et al., *Halenaquinone and xestoquinone derivatives, inhibitors of Cdc25B phosphatase from a Xestospongia sp.*, Bioorganic & Medical Chemistry 13 (2005) pp. 999-1003.

International Search Report for Corresponding PCT Application No. PCT/CA2005/001087 dated Sep. 30, 2005.

Sono, M., et al.,"Enzyme Kinetic and Spectroscopic Studies of Inhibitor and Effector Interactions with Indoleamine 2,3-Dioxygenase. 1. Norharman and 4-Phenylimidazole Binding to the Enzyme as Inhibitors and Heme Ligands", Biochemistry, vol. 28, pp. 5392-5399, (1989).

(Continued)

*Primary Examiner*—Kahsay T Habte
(74) *Attorney, Agent, or Firm*—Christie, Parker & Hale, LLP

(57) ABSTRACT

Inhibitors of indoleamine 2,3-dioxygenase (IDO) are provided as are pharmaceutical compositions containing such inhibitors as well as the use of such inhibitors and compositions for the treatment of a condition in a mammalian subject characterized by pathology of the IDO-mediated tryptophan metabolic pathway. Such conditions may involve suppression of T-cell mediated immune response or may directly result from depletion of tryptophan or accumulation of a product of tryptophan degradation. Specific disease conditions include cataracts, age-related yellowing in the eye, neurodegenerative disorders, mood disorders, cancer and various bacterial/viral infections. IDO inhibitors of this invention are substituted naphthalene and anthracene diones. Novel compounds of this invention include the following taurine-substituted naphthaquinone structure.

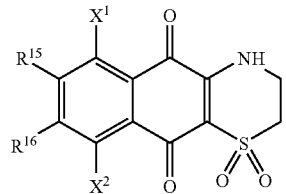

12 Claims, No Drawings

OTHER PUBLICATIONS

Cady, S. G., et al., "1-Methyl-DL-Tryptophan,β-(3-Benzofuranyl)-DL-alanine (the Oxygen Analog of Tryptophan), and , β-[3-Benzo(*b*)thienyl]-DL-alanine(the Sulfur Analog of Tryptophan) Are Competitive Inhibitors for Indoleamine 2,3-Dioxygenase", *Arch. Biochem. Biophys*. vol. 291, pp. 326-333, (1991).

Wirleitner, B., et al., "Interferon-γ-Induced Conversion of Tryptophan: Immunologic and Neuropsychiatric Aspects", *Current Medicinal Chemistry* vol. 10, pp. 1581-1591, (2003).

Takikawa, O., et al., "Regulation of Indoleamine 2,3-Dioxygenase, the First Enzyme in UV Filter Biosynthesis in the Human Lens", *Adv. Exp. Med. Biol*. vol. 467, pp. 241-245, (1999).

Takikawa, O., et al., "Indoleamine 2,3-dioxygenase in the Human Lens, the First Enzyme in the Synthesis of UV Filters", *Exp. Eye Res*. vol. 72, pp. 271-277, (2001).

Swanson K.A., et al., "CDIIc⁺Cells Modulate Pulmonary Immune Responses by Production of Indoleamine 2,3-Dioxygenase", *Am. J. Respir. Cell Mol. Biol*. vol. 30, pp. 311-318, (2004).

Sarkhosh K., et al.,"Immune Cell Proliferation Is Suppressed by the Interferon-γ-Induced Indoleamine 2,3-Dioxygenase Expression of Fibroblasts Populated in Collagen Gel (FPCG)", *J. Cell. Biochem*. vol. 90, pp. 206-217, (2003).

Mellor A..L., et al., "Cutting Edge: Induced Indoleamine 2,3 Dioxygenase Expression in Dendritic Cell Subsets Suppresses T Cell Clonal Expansion", *J. Immunol*. vol. 171, pp. 1652-1655(2003).

Uyttenhove C., et al., "Evidence for a tumoral immune resistance mechanism based on tryptophan degradation by indoleamine 2,3-dioxygenase", *Nat. Med*. vol. 9, pp. 1269-1274, (2003).

Concepcion, G.P., et al., "Antibacterial and Antifungal Activity Demonstrated in Some Philippine Sponges and Tunicates", *Phil. J. Micorbial. Infect. Dis*., vol. 24, pp. 6-19, (1994).

Takikawa, O., et al., "Mechanism of Interferon-γ Action: Characterization of Indoleamine 2,3-Dioxygenase in Cultured Human Cells Induced by Interferon-γ and Evaluation of the Enzyme-Mediated Tryptophan Degradation in its Anticellular Activity", *J. Biol. Chem*. vol. 263, pp. 2041-2048, (1988).

Fahy, E., et al.,"Garveatin A, an Antimicrobial 1 (4H)- Anthracenone Derivative from the Hydroid Garveia annulata", *J. Org. Chem*. vol. 50, pp. 1149-1150, (1985).

Schmitz and Bloor, "Xesto-and Halenaquinone Derivatives from a Sponge, *Adocia sp*., from Truk Lagoon", *J. Org. Chem*. vol. 53, pp. 3922-3925, (1988).

Babizhayev et al., "Efficacy of N-Acetylcarnosine in the Treatment of Cataracts", *Drugs R&D*, vol. 3, pp. 87-103, (2002).

INDOLEAMINE 2,3-DIOXYGENASE (IDO) INHIBITORS

CROSS-REFERENCED TO RELATED APPLICATION(S)

This application is a National Phase Patent Application of International Application Number PCT/CA2005/001087, filed on Jul. 13, 2005, which claims the benefit of the filing date of U.S. Provisional Application No. 60/587,060, filed Jul. 13, 2004.

BACKGROUND

Indoleamine 2,3-dioxygenase (IDO; MW 48,000; EC 1.13.11.42) is a heme-containing enzyme that is the first and rate-limiting enzyme in mammalian tryptophan metabolism. IDO catalyzes the oxidation of the essential amino acid tryptophan to N-formylkynurenine by dioxygen and is responsible for processing tryptophan in the human body. IDO is known to be inhibited in a non-specific manner by general inhibitors of heme-containing enzymes. Also, certain tryptophan (substrate) analogues such as 1-methyl-L-tryptophan (1MT) and beta-(3-benzofuranyl)-DL-alanine are competitive inhibitors of IDO (Sono, M. and Cady, S. G. (1989) Biochemistry 28:5392; and Cady, S. G. & Sono, M. (1991) Arch. Biochem. Biophys. 291:326-333).

Interferon gamma is one of several potent inducers of IDO expression. During persistent immune activation stimulated by high levels of interferon gamma, the availability of free serum tryptophan is diminished by IDO. As a consequence, serotonin production is also reduced. These changes combined with the accumulation of neuroactive kynurenine metabolites such as quinolinic acid (also induced by IDO) contribute to the development of neurologic/psychiatric disorders and is a factor in several mood disorders as well as related symptoms in chronic diseases characterised by IDO activation and tryptophan degradation, such as acquired immune deficiency syndrome (AIDS), Alzheimer's Disease, several types of depression, and cancer. (Wirleitner, Curr. Med. Chem. 10, 1581-91 (2003)).

IDO activity is also involved in the development of age-related nuclear cataracts. IDO is the first and rate-limiting enzyme in UV filter biosynthesis in the ocular lens. UV filter compounds derived from tryptophan degradation (kynurenine and 3-hydroxylkynurenine glucoside) modify proteins present in the human lens. These UV filter adducts increase in amount with age and have been reported (Takikawa et al., Adv. Exp. Med. Biol. 467, 241 (1999)) as responsible for the gradual opacification of the lens known as age-related nuclear cataract. An IDO inhibitor will block this natural process (Takikawa et al., Exp. Eye Res. 72, 271 (2001))

IDO expression is also involved in suppression of the immune response by blocking local T-lymphocyte proliferation. T-lymphocytes are extremely sensitive to tryptophan shortage and arrest in the G1 phase of the cell cycle under conditions of tryptophan depletion. Such suppression of T-cell mediated immune response is a factor in many diseases, including autoimmune diseases, allogenic rejection, neurodegenerative disorders, depression, bacterial infections, viral infections (such as the Human Immunodeficiency Virus (HIV)) and cancer (Swanson et al., Am. J. Respir. Cell Mol. Biol. 30, 311 (2003); Sarkhosh et al., J. Cell. Biochem. 90, 206 (2003); Mellor et al., J. Immunol. 171, (2003); and Wirleitner et al. Current Medicinal Chemistry, 10, 1581-1591 (2003)). IDO inhibitors are useful for regulation of T-cell mediated immune responses (U.S. Pat. No. 6,482,416, U.S. Pat. No. 6,451,840 and Munn et al. U.S. 2004/0234623) Also, IDO activity in the placenta is important in preventing allogenic rejection of a fetus as exemplified by fetus rejection upon administration of the IDO inhibitor 1-methyl-L-tryptophan (1MT).

Most human tumors have been found to express IDO constituitively. Mouse tumor cells from preimmunized mice have been shown to protect themselves against rejection by expressing IDO; an effect that is abrogated by administration of 1MT. Efficacy of cancer therapies would then be improved by concomitant administration of an IDO inhibitor. (Uyttenhove et al., Nat. Med. 9, 1269-1274 (2003); Prendergast et al. WO 2004/094409 and WO 2004/093871; and Munn et al. U.S. 2004/0234623).

IDO inhibitors would be useful for suppression of mood disorders and for treatment of other diseases characterised by pathology of the IDO mediated tryptophan metabolic pathway, including viral infections such as in AIDS, bacterial infections such as in Lyme disease and Streptococcal infections, neurodegenerative disorders (e.g. Alzheimer's, Huntington's and Parkinson's Diseases), depression, cancer (including T-cell leukemia and colon carcinoma), conditions of the eye (e.g. cataracts and age-related yellow) and autoimmune disorders.

SUMMARY

This invention is based in part on the discovery that a wide range of dione substituted naphthalene and anthracene diones function as IDO inhibitors and in many cases, such inhibition is non-competitive. Such compounds were not previously known as IDO inhibitors although some had been noted for certain cytotoxic or antibiotic activities in vitro. Having now determined a mechanism of action for such compounds, it is now known that such compounds are useful for in vivo treatment or prophylaxis of diseases in mammalian subjects which are characterized by pathology of the IDO-mediated tryptophan metabolic pathway. Thus, these compounds are now made available for use in treatment or prophylaxis of disease conditions which result from the products of tryptophan degradation (e.g. cataracts and age-related yellowing in the eye) as well as disease conditions which result from IDO-mediated depletion of tryptophan such as those which involve suppression of T-cell mediated immune responses (e.g. cancer and various bacterial/viral infections). Further such compounds may also be used in the treatment or prophylaxis of other disease conditions which relate to depletion of tryptophan such as mood disorders, depression, anxiety and neurodegenerative disorders. None of these uses are made apparent by previous knowledge that certain compounds are capable of killing or inhibiting cell growth in vitro.

The invention contemplates the use of the compounds described herein, including their tautomeric forms, as well as their structural analogues, their pharmaceutically acceptable salts and pharmaceutically acceptable compositions comprising at least one such compound, analogue or salt, for inhibition of IDO and in the treatment or prophylaxis of diseases characterized by the pathology of the IDO-mediated tryptophan metabolic pathway. Such diseases include but are not limited to neoplastic diseases, cancer, diseases of the eye, cataracts, autoimmune diseases, mood disorders, depression and anxiety. Use includes in vivo and in vitro applications as well as use in the manufacture of medicaments and IDO inhibitory agents and compositions.

The invention also provides novel substituted naphthaquinones and naphthalenes obtainable by synthesis or isolation from extracts of the marine hydroid Garveia annulata and the marine sponge *Xestospongia*, structural analogues and derivatives thereof and pharmaceutically acceptable salts thereof, as well as pharmaceutically acceptable compositions containing at least one of such substituted naphthaquinones, naphthalenes, structural analogues or derivatives and salts thereof.

Methods of isolating compounds of the invention from natural sources and methods for syntheses are provided. Once extracted or synthesized, methods for their use are also provided.

DETAILED DESCRIPTION

Various embodiments of this invention involve at least one compound selected from one of the formulas I, II, III, IV, or V shown below, including tautomeric forms, as well as pharmaceutically acceptable salts thereof. Also involved are compositions comprising at least one such compound or salt and a suitable carrier, diluent or adjuvant, for the treatment of diseases characterized by the pathology of the IDO-mediated tryptophan metabolic pathway.

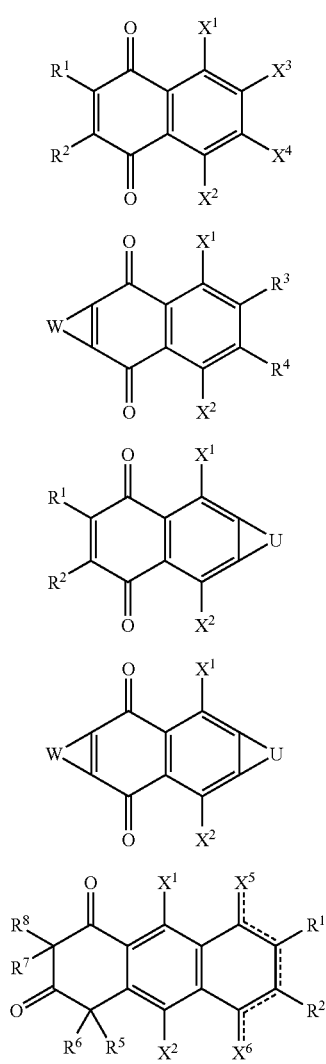

$X^1$, $X^2$, $X^3$, $X^4$, $X^5$ and $X^6$ are independently selected from the following group: H, R, OH, OR, F, Cl, Br, I, $NH_2$, NHR, $NR_2$, CN, SH, SR, $SO_3H$, $SO_3R$, $SO_2R$, $OSO_3R$, and $NO_2$, additionally $X^5$ and $X^6$ may be independently oxo (=O). R is an optionally substituted saturated or unsaturated linear, branched, or cyclic alkyl group or optionally substituted aryl group, where optional substitution of R can refer to the presence of substituents selected from aryl, ether, amino, hydroxy, ester, thioether, thiol, nitrile, nitro, amide, carbonyl, carboxyl, carboxylate, and halide groups. Where R is an aryl group, or is substituted by an aryl group, the aryl group can be optionally substituted with ether, amino, hydroxy, ester, thioether, amide, nitro, carbonyl, carboxyl, carboxylate, and halide groups.

$R^1$, $R^2$, $R^3$, $R^4$, $R^5$, $R^6$, $R^7$ and $R^8$ are independently selected from the group consisting of: H, OH, OR, and a linear, branched, or cyclic, saturated or unsaturated alkyl group, where one or more carbon atoms of the alkyl backbone are optionally and independently substituted or may be replaced by oxygen (O) or sulfur (S) atoms or secondary amino (NR) groups. Optional substituents may be selected from aryl, ether, amino, hydroxy, ester, thioether, thiol, nitrile, nitro, amide, carbonyl, carboxyl, carboxylate, and halide groups. R is as defined above.

W is a group of atoms that complete a substituted or unsubstituted 5, 6, or 7 membered ring containing C, O, N, or S atoms, fused to the naphthquinone nucleus of formulas II or IV. Examples of W are shown as structures (a) to (e) below, with $X^7$ having the same definition as $X^1$-$X^4$ defined above. In each case, all regioisomers which are formed by the fusion of W in the orientation shown or when inverted, are included.

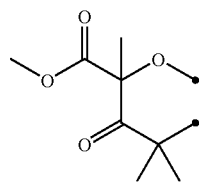

(a)

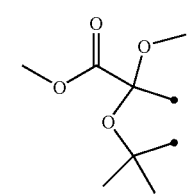

(b)

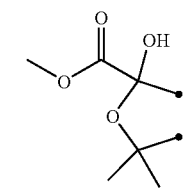

(c)

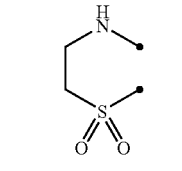

(d)

(e)
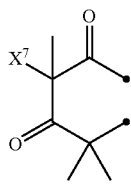

(k)
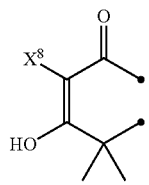

U is a group of atoms that complete a substituted or unsubstituted, aromatic or non-aromatic, mono-, bi- or tri-cyclic ring system containing C, O, N or S atoms, fused to the naphthaquinone nucleus of formulas II and IV. Examples of U are shown below as structures (f) to (k), with $X^8$ having the same definition as $X^7$ above. Again, all regioisomers are included.

(f)

(g)

(h)

(i)

(j)

Some embodiments of this invention involve at least one compound selected from a structure shown in Table 1, and tautomeric forms thereof, their pharmaceutically-acceptable salts, as well as pharmaceutically acceptable compositions comprising such a compound or salt, for the treatment of diseases characterized by the pathology of the IDO-mediated tryptophan metabolic pathway.

TABLE 1

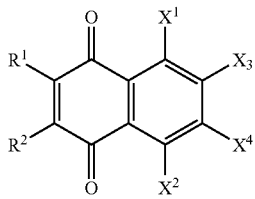

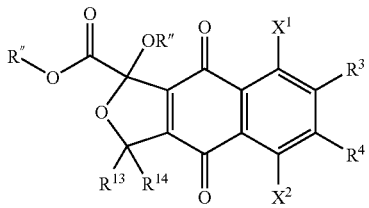

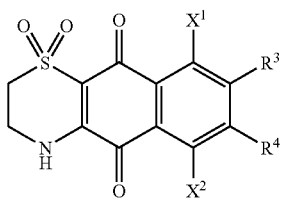

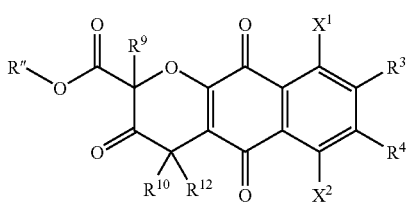

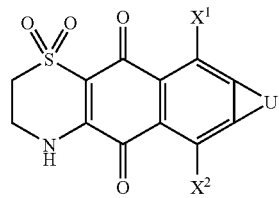

TABLE 1-continued

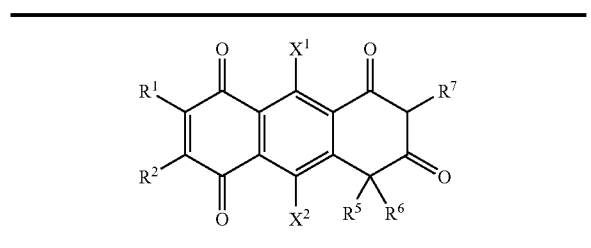

In Table 1, substituents identified as $R^1$ to $R^7$, $X^1$ to $X^4$ and U are as defined above. Each $R^{11}$ may be the same or different and has the definition as R, above. Each of $R^9$, $R^{10}$, $R^{12}$, $R^{13}$ and $R^{14}$ have the same definition as $R^1$ to $R^7$.

Of the embodiments of this invention described above, certain embodiments of particular interest are of formula II or IV in which W has structure (d) shown above. Thus, these compounds of particular interest are described by the following formula and include tautomeric forms thereof.

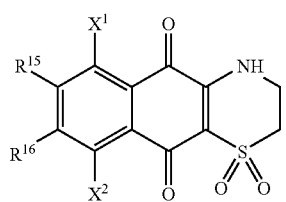

VI

Compounds of formula VI are novel except for the following individual compounds described in Schmitz et al. *J. Org. Chem.* (1988) 53, 3922-3925 and Concepcion, G. P. et al. *Phil. J. Micorbial. Infect. Dis.* (1994), 24, 6-19.

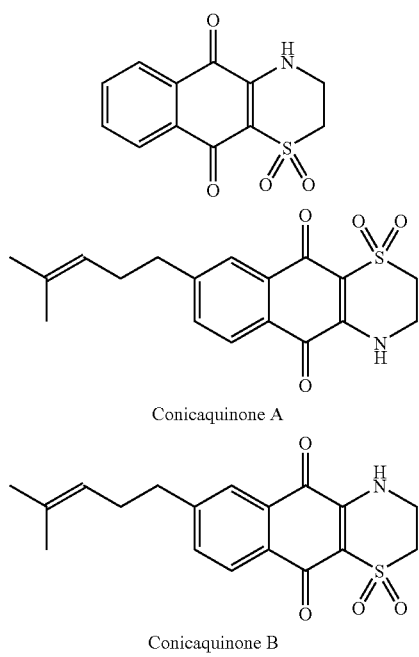

Conicaquinone A

Conicaquinone B

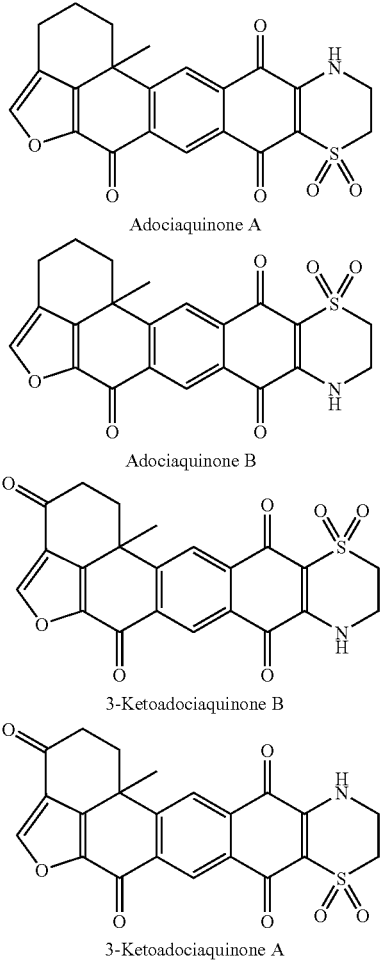

Adociaquinone A

Adociaquinone B

3-Ketoadociaquinone B

3-Ketoadociaquinone A

In formula VI, $X^1$ and $X^2$ are as defined above. $R^{15}$ and $R^{16}$ may be individual substituents or may be fused as a single group. When $R^{15}$ and $R^{16}$ are individual substituents, they independently have same definition as $R^3$ and $R^4$ above. When $R^{15}$ and $R^{16}$ are fused, they together have the same definition as U above.

Compounds of formula VI include compounds having the following structure and tautomeric forms thereof.

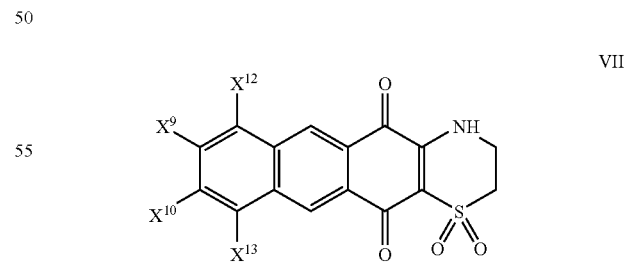

VII $X^9$ and $X^{13}$ independently have the same definition as $X^1$ and $X^2$ above.

In some embodiments of this invention, one or more of $X^1$-$X^{13}$ and $R^1$-$R^{16}$ may be independently selected in a manner consistent with the above definitions from the group consisting of: H, $C_1$ to $C_6$ alkyl, OH, COOH, C(O)R, COOR and halogen, with R being as described above. Also, in some embodiments, one or both of $X^5$ and $X^6$ may be oxo.

In some embodiments, substituents $R^1$ to $R^{16}$ are selected from the group consisting of H, OH, $C_1$-$C_3$ alkyl and $C_1$-$C_3$ alkoxy; substituents $X^1$ to $X^4$ and $X^7$ to $X^{13}$ are selected from the group consisting of H, OH, $C_1$-$C_3$ alkyl, $C_1$-$C_3$ alkoxy and halogen; and substituents $X^5$ and $X^6$ are selected from the group consisting of H, OH, $C_1$-$C_3$ alkyl, $C_1$-$C_3$ alkoxy and oxo.

Particular embodiments of the invention may utilize at least one compound selected from the compounds depicted in Table 2 and Table 3 below, and their tautomeric forms thereof, pharmaceutically acceptable salts, and compositions of the at least one such compound or its pharmaceutically acceptable salt and a pharmaceutically acceptable suitable carrier, diluent or adjuvant, for the treatment of diseases characterized by the pathology of the IDO-mediated tryptophan metabolic pathway. Preferably, a compound selected for use in this invention will be one which exhibits a $K_i$ value in an IDO inhibition assay of a micromolar concentration or less. More preferably, the $K_i$ value will be in the nanomolar range or less. Some known substrate analog inhibitors of IDO are reported to have $K_i$ values in the micromolar range.

This invention also provides novel compounds from within formulas I, II, III, IV, and V, novel salts thereof, and pharmaceutically acceptable compositions comprising an acceptable carrier (with substituents as defined herein) which novel compounds exclude those depicted in Table 2 or otherwise known in the art.

The invention also provides the novel compounds depicted in Table 3, and their tautomeric forms as well as pharmaceutically acceptable salts thereof, and compositions comprising a pharmaceutically acceptable carrier and at least one such compound or salt thereof.

TABLE 2

Annulin A

Annulin B

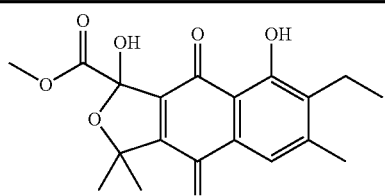

Garveatin A

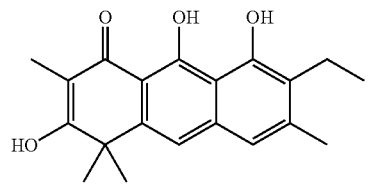

Garveatin B

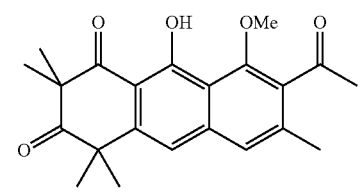

Garveatin C

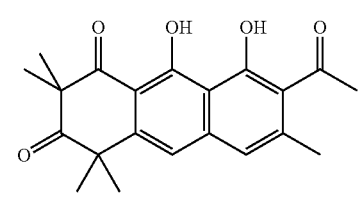

Garveatin D

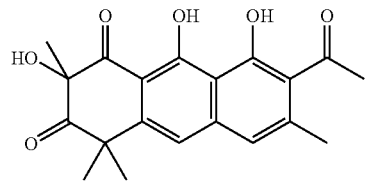

2-hydroxyGarveatin A

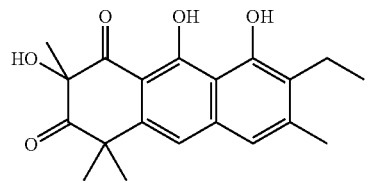

2-hydroxyGarveatin B

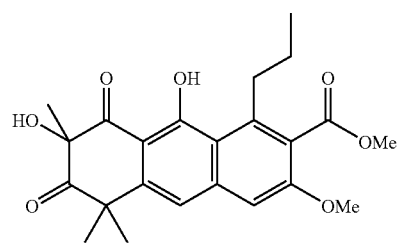

2-hydroxygarvin A

TABLE 2-continued
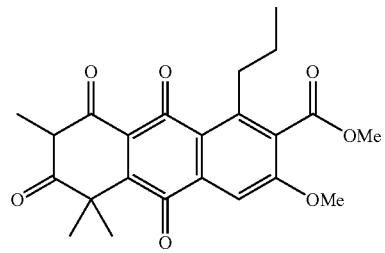
Garvin A quinone
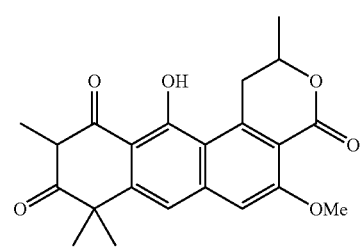
Garvin B
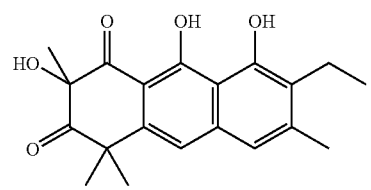
2-hydroxyGarvcatin B
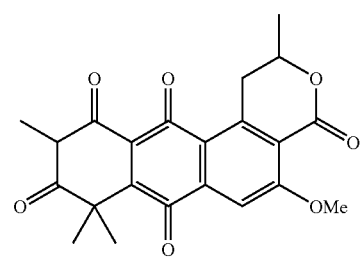
Garvin B quinone
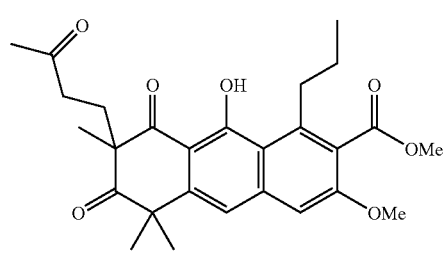
Garvalone B
TABLE 2-continued
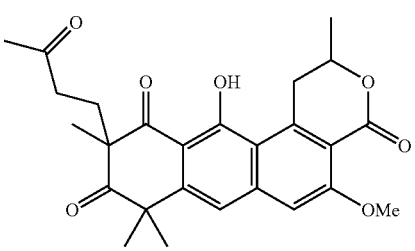
Garvalone B
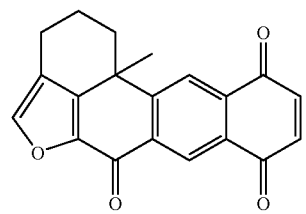
Xestoquinone
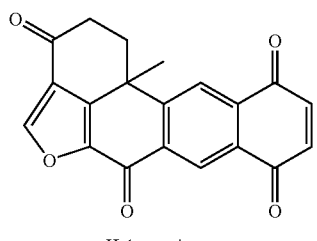
Helenaquinone
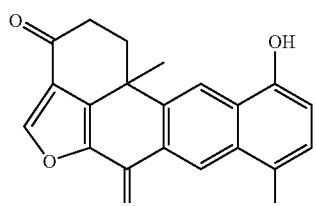
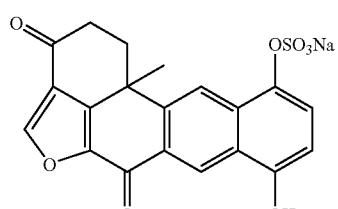
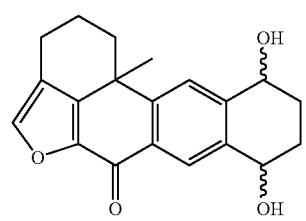

TABLE 2-continued
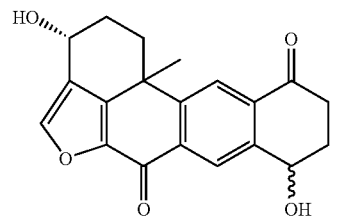
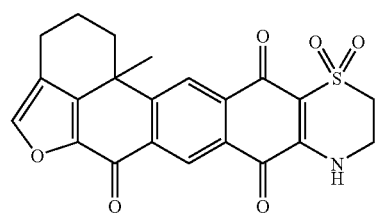
Adociaquinone B
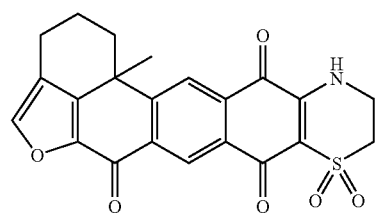
Adociaquinone A
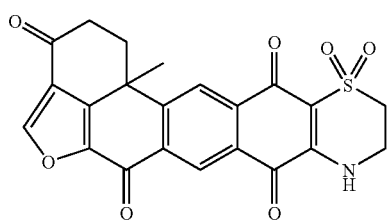
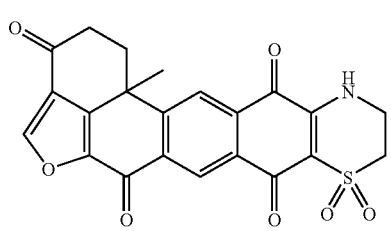
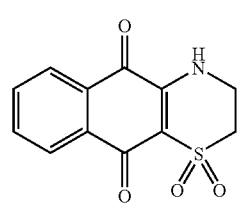
TABLE 2-continued
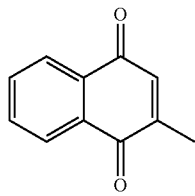
Menadione (Vitamin K3)
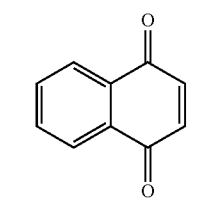
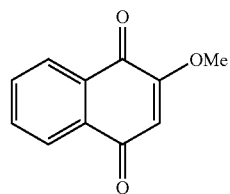
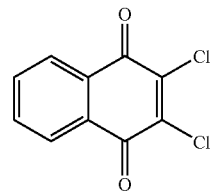
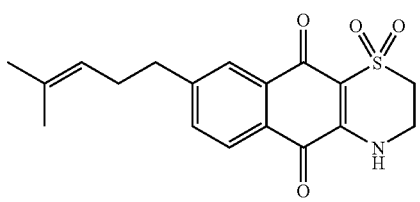
Conicaquinone A
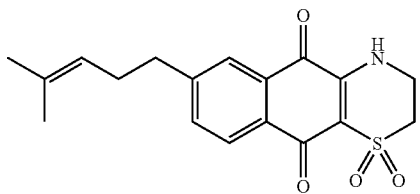
Conicaquinone B
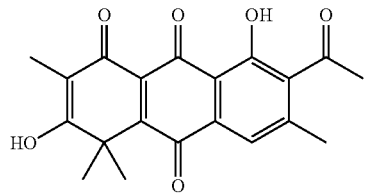
Garveatin A quinone

TABLE 2-continued
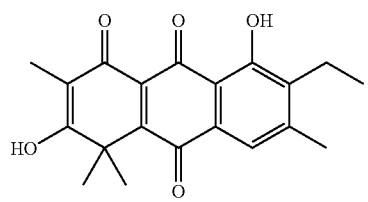
Garveatin B quinone
TABLE 3
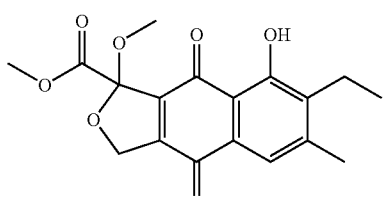
Annulin C
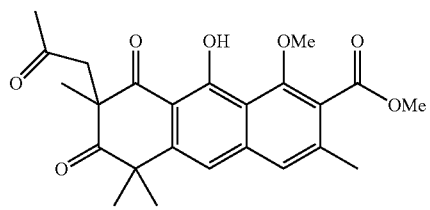
Garvalone C
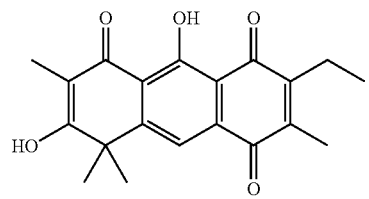
Garveatin E
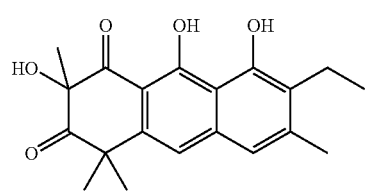
Garveatin F
TABLE 3-continued
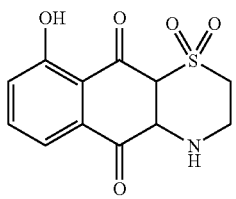
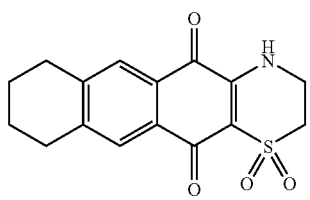
Compounds described herein may be synthesised using protocols adopted from the art, including the following exemplary schemes.
Scheme I
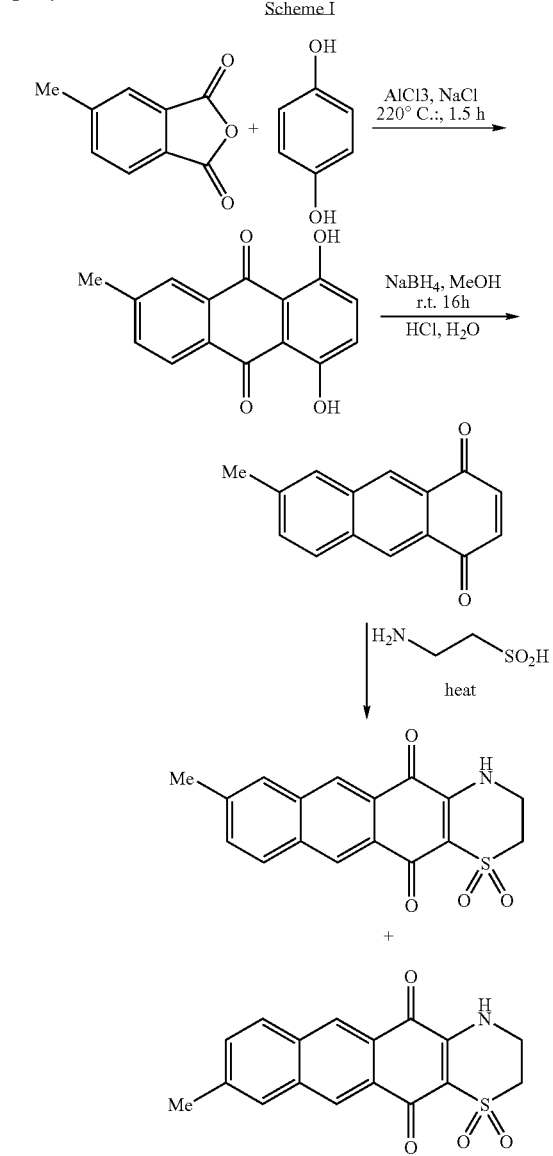

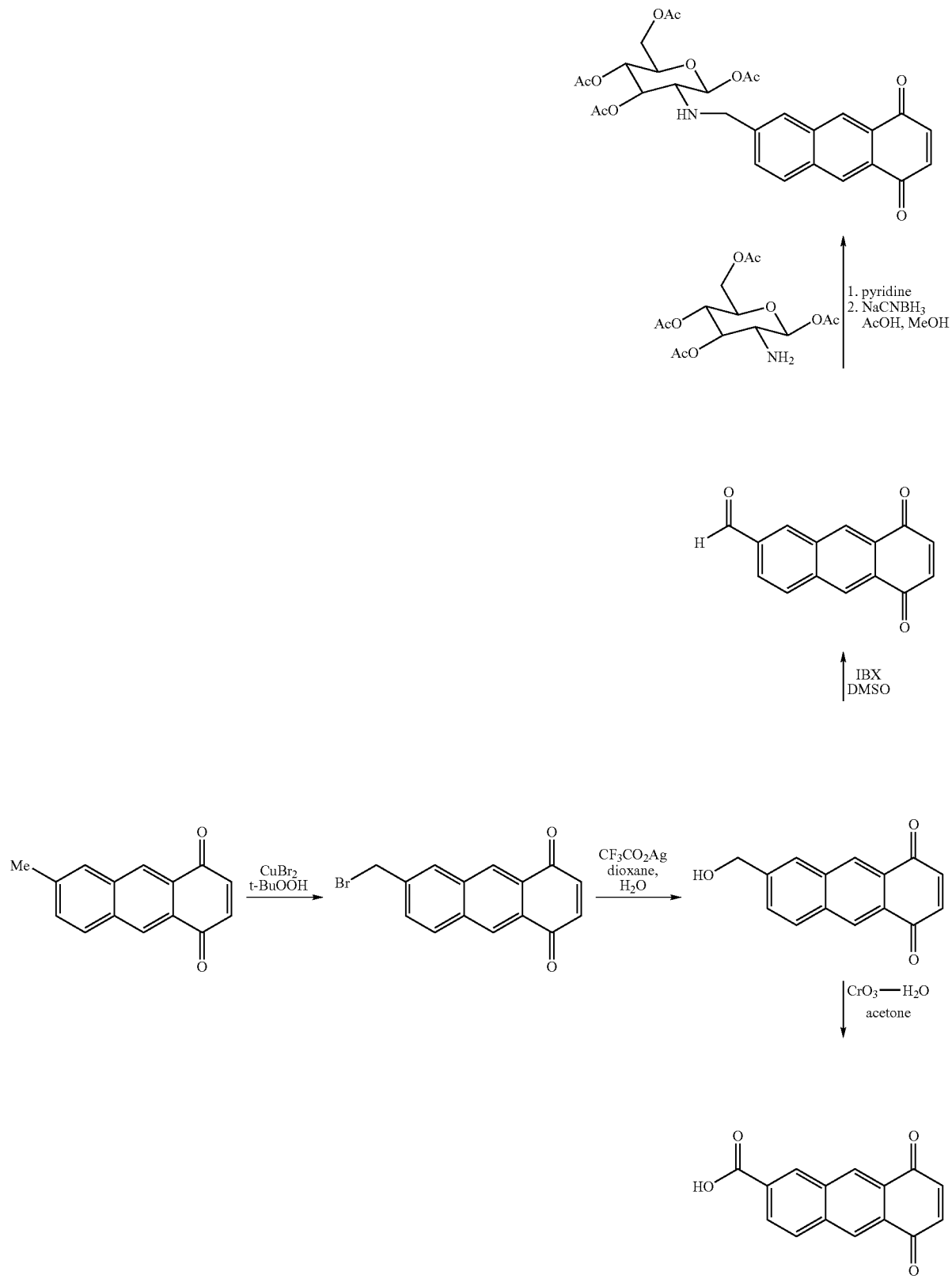

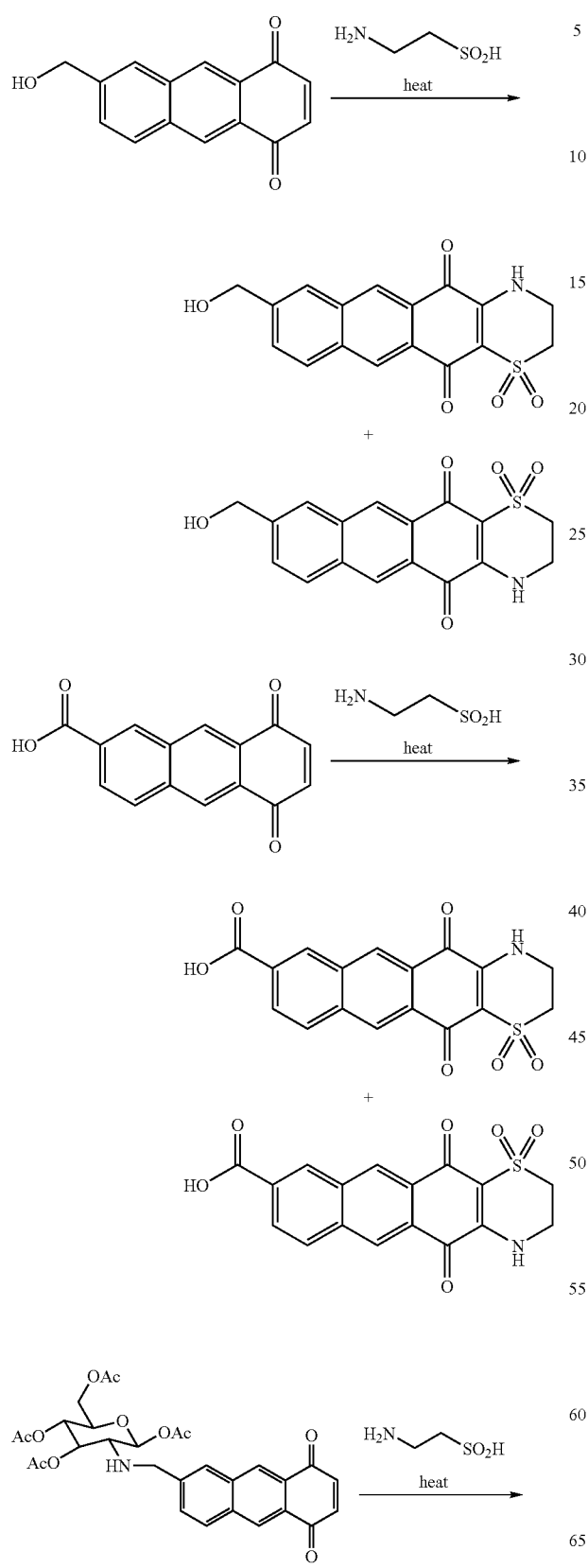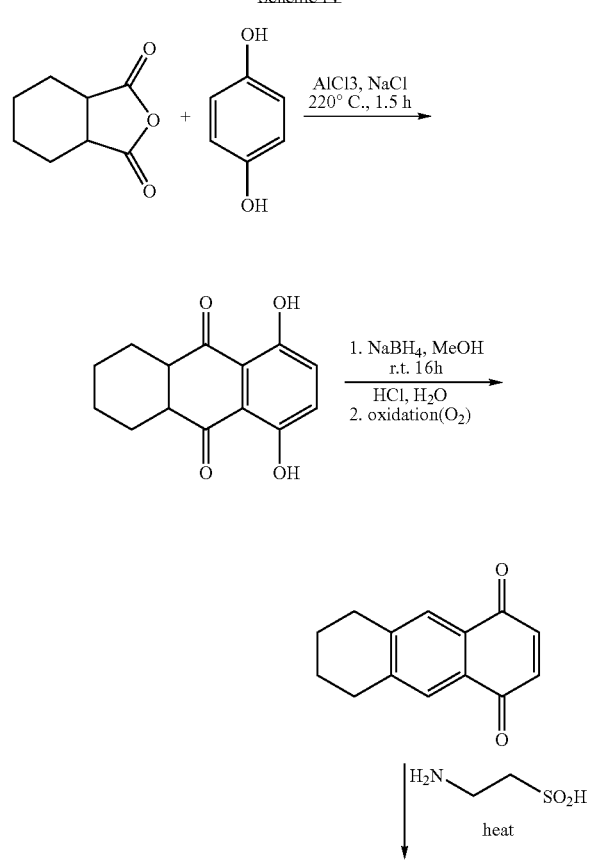

-continued

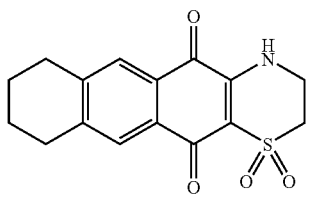

Using theses reaction mechanisms, one of skill in the art would be able to prepare a compound described herein. For example, a specific synthesis of Adociaquinones A and B may be found in Harada et al. *Tetrahedron: Asymmetry* 6 375-376 (1995). A specific synthesis of Conicaquinones A and B may be found in Aiello et al. *Eur. J. Org. Chem.* 898-900 (2003).

Some compounds of this invention may be isolated from natural sources such as the marine hydroid *Garveia annulata* (Fahy et al. *J. Org. Chem.* 51, 5145-5148 (1986); and Fahy et al. *J. Org. Chem.* 51, 57-61 (1986)). *Garveia annulata* may be collected by hand using SCUBA in Barkley Sound, British Columbia, Canada during the winter and spring months. *Garveia annulata* is a brilliant orange hydroid that is commonly encountered in rocky subtidal habitats from Alaska to Southern California during winter and spring. Isolation of compounds from *Garveia annulata* may be achieved using the following methanol extraction procedure.

Freshly collected whole specimens of *Garveia annulata* are placed in methanol and may be stored at room temperature. The methanol extract is then decanted and filtered through Celite™. The filtrate is evaporated in vacuo to give an aqueous suspension that is diluted to 400 mL with distilled water and extracted successively with hexane (3×400 mL), methylene chloride (3×400 mL), and ethyl acetate (2×400 mL).

The hexane (600 mg) and methylene chloride (4 g) extracts are fractionated separately by step-gradient vacuum flash chromatography using 3.5-cm-think silica pad in a sintered-glass funnel (10 cm diameter). Fractions eluting with the same solvent composition from each separation are combined. Elution with 20% ethyl acetate/hexane, 50% ethyl acetate/hexane, 100% ethyl acetate/hexane, and 20% methanol/ethyl acetate give fractions A (140 mg), B (500 mg), C (1.5 g), and D (700 mg), respectively.

Flash fractions may be evaporated to dryness and chromatographed on LH20 (90% methanol/methylene chloride; 1 m×4 cm column). Preparative silica gel TLC of any major peaks resulting from the LH20 chromatography may yield fractions and these fractions may be further purified using TLC. A final purification of any compounds may be achieved using normal-phase HPLC.

Some compounds may be isolated from pacific sponges of the genus *Xestospongia* (Schmitz et al. *J. Org. Chem.*, 53, 3922-3925)). *Xestospongia* may be collected by hand using SCUBA from the Eten Island area of Truk Lagoon from November to January at depths of about 5-10 m. *Xestospongia* may also be found around Papua New Guinea. Isolation of compounds from *Xestospongia* may be achieved using the following extraction procedure.

Freshly collected samples of *Xestospongia* may be frozen within a few hours of collection. The frozen specimens may be soaked in CHCl$_3$/MeOH (1:1) for 1 day and then again in CHCl$_3$/MeOH (2:1). The combined solutions are concentrated under reduced pressure, and the concentrate is partitioned between CHCl$_3$ and 30% aqueous MeOH. The chloroform solubles are then chromatographed into fractions. The extraction time in the solvent bath may be varied from 12 hours to 2 days and the extraction solvent may be methanol, chloroform or n-hexane.

Various in vitro assays (see for example Takikawa, et al. *J. Biol. Chem.* 263, 2041-2048 (1988)) may be used to screen (e.g. high-throughput screening) or test reaction products or extracts obtained natural sources for IDO inhibition activity or to determine the kinetics of IDO inhibition. For example, IDO activity may be assayed by means of a reaction mixture (100 microlitre total volume) containing potassium phosphate buffer (50 mM, pH 6.5), ascorbic acid (20 mM), catalase (200 microgram/mL), methylene blue (10 mM), L-tryptophan (400 mM), and purified, human IDO. The reaction shown below may be allowed to proceed for 40 min (37° C.) and stopped by the addition of 20 microlitre of 30% (w/v) trichloroacetic acid. The N-formyl kynurenine formed from tryptophan in the reaction mixture during this time is then converted to kynurenine by incubating the reaction mixture at 65° C. for 15 minutes. After cooling the reaction mixture to room temperature, an equal volume of 2% (w/v) p-dimethylamino benzaldehyde in acetic acid may be added to convert the kynurenine present in the reaction mixture to a yellow adduct that can be detected at 480 nm. A standard curve for this latter reaction may be constructed with the use of standard solutions prepared from authentic L-kynurenine. Protein concentration may be determined by the Coomassie blue dye-binding method of Bradford with bovine serum albumin as a standard. (Takikawa et al, *J. Biol. Chem.* 263, 2041-2048).

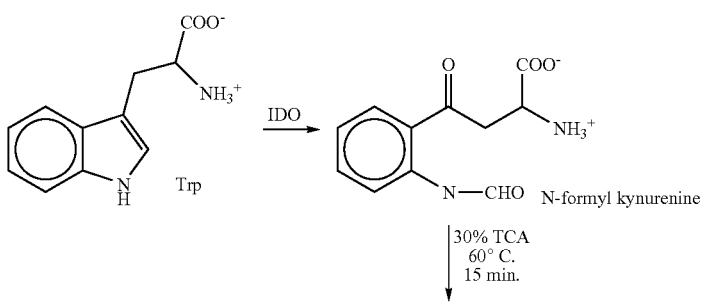

-continued

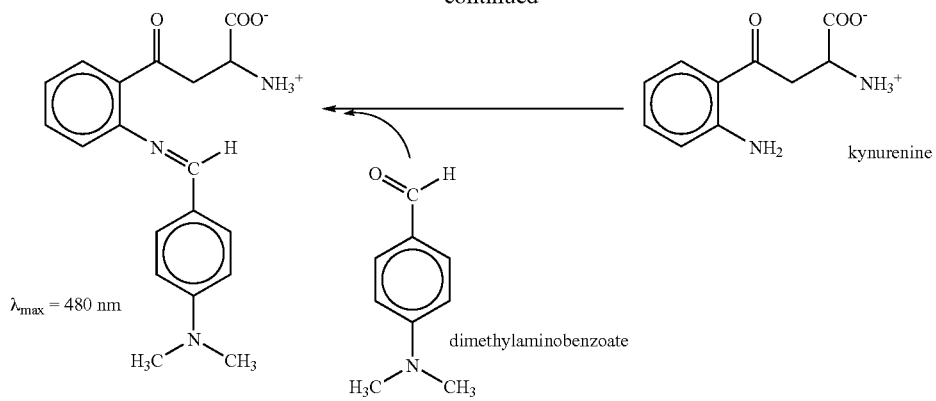

Crude extracts from the marine hydroid *Garveia annula* collected in British Columbia and the sponge *Xestospongia* sp. collected in Papua New Guinea show activity in the aforementioned assay. Bioassay guided fractionation will identify annulins A, B, and C, garveatins A, C, E, and F, and 2-hydroxygarvin A as active IDO inhibitors from *Garveia annulata* extracts. Annulins A and B, garveatins A and C, and 2-hydroxygarvin A have been previously reported (Fahy et al *J. Org. Chem.*, (1985), 50, 1149-50; *J. Org. Chem.*, (1986), 51, 57-61; *J. Org. Chem.*, (1986), 51, 5145-48; *Can. J. Chem.*, (1987), 65, 376-83), but were not known to be IDO inhibitors. Annulin C, Garvalone C and garveatins E and F are novel. Similarly, xestoquinone, adociaquinone A, and adociaquinone B are identified as active IDO inhibitors from *Xestospongia* extracts. Xestoquinone, adociaquinone A, and adociaquinone B had been previously isolated from sponge extracts and their structures have been reported in the literature (Schmitz and Bloor *J. Org. Chem.* (1988), 53, 3922-3925), but were not known as IDO inhibitors. Various naphthaquinone analogs of the *Garveia* and *Xestospongia* natural products are available and also and also exhibited inhibition activity. In this way, menadione (also known as vitamin $K_3$) is shown to be an IDO inhibitor, which was not previously known.

IDO plays a role in several diseases, including *Clamydia psittaci* infection and *Streptococcus pyogenes* infection, systemic lupus erythematosus, rheumatoid arthritis, Alzheimer's disease, Huntington's disease, Parkinson's disease, lyme neuroborreliosis, late lyme encephalopathy, Tourette's syndrome, systemic sclerosis, multiple sclerosis, coronary heart disease, T-cell mediated immune diseases, chronic infections (viral, bacterial, fungal and microbial), depression, neurological disorders, cancer tumors, and cataracts. Inhibitors of IDO may be used to treat these diseases. Other diseases that IDO inhibitors may be used to treat include, but are not limited to, human immunodeficiency virus (HIV), AIDS-related cancers, adrenocorticocancer, basal cell carcinoma, bladder cancer, bowel cancer, brain and CNS tumors, breast cancers, B-cell lymphoma, carcinoid tumors, cervical cancer, childhood cancers, chondrosarcoma, choriocarcinoma, chronic myeloid leukemia, rectal cancers, endocrine cancers, endometrial cancer, esophageal cancer, Ewing's sarcoma, eye cancer, gastric cancer or carcinoma, gastrointestinal cancers, genitourinary cancers, glioma, gynecological cancers, head and neck cancers, hepatocellular cancer, Hodgkins disease, hypopharynx cancer, islet cell cancer, Kaposi's sarcoma, kidney cancer, laryngeal cancer, liver cancer, lung cancer (including small-cell lung carcinoma and non-small-cell carcinoma), lymphoma, male breast cancer, melanoma, mesothelioma, multiple myeloma, nasopharyngeal cancer, neuroblastoma, non-Hodgkins lymphoma, non-melanoma skin cancer, osteosarcoma, ovarian cancer, pancreas cancer, pituitary cancer, prostate cancer, renal cell carcinoma, retinoblastoma, rhabdomyosarcoma, sarcoma, skin cancer, squamous cell carcinoma, stomach cancer, testicular cancer or seminoma, thymus cancer, thyroid cancer, transitional cell cancer, trophoblastic cancer, uterine cancer, vaginal cancer, Waldenstrom's macroglobulinemia, and Wilm's tumor, colorectum, cervix, endometrium, ovary, testis, mesothelial lining, white blood cell (including lymphoma and leukemia) esophagus, muscle, connective tissue, adrenal gland, bone, glioblastoma, and cutaneous basocellular carcinoma.

Many compounds of this invention or for use in this invention are generally water soluble and may be formed as salts. In such cases, pharmaceutical compositions in accordance with this invention may comprise a salt of such a compound, preferably a physiologically acceptable salt, which are known in the art. Pharmaceutical preparations will typically comprise one or more carriers acceptable for the mode of administration of the preparation, be it by injection, inhalation, topical administration, lavage, or other modes suitable for the selected treatment. Suitable carriers are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The table or capsule may be enteric coated, or in a formulation for sustained release. Many suitable formulations are known, including, polymeric or protein microparticles encapsulating a compound to be released, ointments, gels, hydrogels, or solutions which can be used topically or locally to administer a compound. A sustained release patch or implant may be employed to provide release over a prolonged period of time. Many techniques known to skilled practitioners are described in *Remington: the Science & Practice of Pharmacy* by Alfonso Gennaro, $20^{th}$ ed., Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel. Munn et al. (U.S. Pat. Nos. 6,451,840 and 6,482,416) describe administering to a subject an effective amount of a pharmaceutical composition comprising an inhibitor of IDO, and uses thereof.

Ophthalmic compositions such as sterile aqueous solutions may be prepared using techniques known in the art by the skilled practitioner. Pigiet et al. (U.S. Pat. No. 4,771,036) describe a method and an ophthalmic composition for the prevention and reversal of cataracts. Itoh et al. (U.S. Pat. No. 6,500,813) describe ophthalmic compositions, including eye drops, used for preventing deterioration of the optical transparency. Babizhayev et al. *Drugs R&D*, 3, 87-103 describe a human trial of eye drops containing drugs in a phosphate-buffered saline for the treatment of cataracts. Ophthalmic compositions may be packaged in a suitable container or eye dropper adopted for the delivery of drops to the eye.

Compounds described herein may be used in combination with chemotherapeutics or other therapeutic modalities, particularly for the treatment of a cancer. Other therapeutic modalities include, but are not limited to, chemotherapeutics, radiation therapy, antiviral agents, antibacterial agents, antifungal agents, antimicrobial agents, signal transduction inhibitors, cytokines, vaccines, hormone therapy, surgical resection, immunostimulatory therapy, anti-tumor vaccines, antibody based therapies, whole body irradiation, bone marrow transplantation and peripheral blood stem cell transplantation. An IDO inhibitor may be administered before, after or during the other therapeutic modality.

As used herein, a "chemotherapeutic" refers to a chemical compound or composition that may be used to treat a disease in a patient. There are many chemotherapeutics and of particular interest are cancer chemotherapeutics.

There are many groups of cancer chemotherapeutics including, alkylating and oxidizing agents, antimetabolites, antibiotics, mitotic inhibitors, chromatin function inhibitors, hormone and hormone inhibitors, antibodies, immunomodulators, angiogenesis inhibitors, rescue/protective agents, and others.

The alkylating and oxidizing agent class of cancer chemotherapeutics includes seven subclasses: nitrogen mustards, ethylenimines, alkyl sulfonates, nitrosureas, triazenes and platinum coordinating complexes. Examples of nitrogen mustards include mechlorethamine (Mustargen™), cyclophosphamide (Cytoxan™ and Neosar™), ifosfamide (Ifex™), phenylalanine mustard, melphalan (Alkeran™), chlorambucol (Leukeran™), uracil mustard and estramustine (Emcyt™). An example of an ethylanimine is thiotepa (Thioplex™). An example of an alkyl sulfonate is busulfan (Myerlan™). Examples of nitrosureas are lomustine (CeeNU™), carmustine (BiCNU™ and BCNU™) and streptozocin (Zanosar™). Examples of triazines are dicarbazine (DTIC-Dome™) and temozolamide (Temodar™). Examples of platinum coordination complexes are cis-platinum, cisplatin (Platinol™ and Platinol AQ™) and carboplatin (Paraplatin™). Other examples of alkylating and oxidizing agents include altretamine (Hexalen™) and arsenic (Trisenox™). This class of chemotherapeutics are generally cell cycle non-specific (although a greater effect in the G1, S phase of the cell cycle is often observed) and work through the alkylation of DNA (through carbonium ion intermediates). They may encourage covalent cross-linking of DNA, RNA and proteins, cause single-stranded DNA breaks or provide abnormal DNA base pairing. Through these mechanisms these chemotherapeutics tend to interrupt cell replication. In particular, platinum coordinating complex agents generally cause cross-linking of DNA strands and have an affinity for alkylation at guanine bases (at the N7 position) and adenine (at the N7 position). This may cause interstrand and intrastrand cross-linking. The drugs themselves may also bind to protein SH groups.

The antimetabolite class of cancer chemotherapeutics includes: folic acid analogs, pyrimidine analogs and purine analogs. Examples of folic acids include: methotrexate (Amethopterin™, Folex™, Mexate™, Rheumatrex™). Examples of pyrimidine analogs include 5-fluoruracil (Adrucil™, Efudex™, Fluoroplex™), floxuridine, 5-fluorodeoxyuridine (FUDR™), capecitabine (Xeloda™), flurdarabine (Fludara™), cytosine arabinoside (Cytaribine™, Cyrosarm, ARA-C™). Examples of purine analog include: 6-mercaptopurine (Purinethol), 6-thioguanine (Thioguanine™), gemcitabine (Gemzar™), cladribine (Leustatin™), deoxycoformycin and pentostatin (Nipent™). These chemotherapeutics are generally S phase specific and are often structurally related to normal cellular components. They often work through interference with nucleotide syntheses and compete with cellular nucleotides in DNA and RNA synthesis.

The antibiotic class of cancer chemotherapeutics includes: doxorubicin (Adriamycin™, Rubex™, Doxil™, Daunoxome™-liposomal preparation), daunorubicin (Daunomycin™, Cerubidine™), idarubicin (Idamycin™), valrubicin (Valstar™), epirubicin, mitoxantrone (Novantrone™), dactinomycin (Actinomycin D™, Cosmegen™), mithramycin, plicamycin (Mithracin™), mitomycin C (Mutamycin™), bleomycin (Blenoxane™), procarbazine (Matulane™). chemotherapeutics in this class are also generally cell cycle non-specific (exceptions include bleomyacin and procarbozine). This class of chemotherapeutics generally intercalates into double-stranded DNA and disrupts the DNA by binding to the DNA helix. These chemotherapeutics also inhibit DNA synthesis by inhibiting nucleotide incorporation or inhibiting DNA dependent RNA synthesis. Some of these chemotherapeutics also inhibit DNA coiling and in some cases achieve this by inhibiting topoisomerase II which leads to strand breaks. In particular, doxorubicin intercalates in DNA, binding to the sugar phosphate backbone of the DNA. Doxorubicin also binds to cell membranes blocking the phosphatidylinositol activation. Doxorubicin can also inhibit topoisomerase II.

The mitotic inhibitor class of cancer chemotherapeutics includes: taxanes or diterepenes and vinca alkaloids. Examples of taxanes include paclitaxel (Taxol™) and docetaxel (Taxotere™). Examples of vinca alkaloids include vinblastine sulfate (Velban™, Velsar™, VLB™), vincristine sulfate (Oncovin™, Vincasa PFS™, Vincrex™) and, vinorelbine sulfate (Navelbine™). This class of chemotherapeutics are cell cycle specific and generally disrupt the cell cycle during the M phase. This class of cancer chemotherapeutic disrupts the mitotic spindle thereby inhibiting chromosomal segregation and blocking mitosis. The taxanes groups of mitotic inhibitors, which include paclitaxel and docetaxel, are derived from the bark of the Pacific Yew tree. They prevent microtubular depolymerization thereby inhibiting a reorganization of the microtubular network. Microtubular stabilization also promotes the formation of abnormal bundles of microtubules.

The chromatin function inhibitor class of cancer chemotherapeutics includes: camptothecins and epipodophyllotoxins. Examples of camptothecins include topotecan (Camptosar™) and irinotecan (Hycamtin™). Examples of epipodophyllotoxins include etoposide (VP-16™, VePesid™ and Toposar™) and teniposide (VM-26™ and Vumon™). These chemotherapeutics are generally cell cycle specific and may bind to either topoisomerase I or topoisomerase II. In the case where they bind to topoisomerase I, this prevents religation of breaks in the DNA. In the case where they bind with topoisomerase II, this prevents transcription replication of the DNA thereby killing the cell.

The hormone and hormone inhibitor class of cancer chemotherapeutics includes: estrogens, antiestrogens, aromatase inhibitors, progestins, GnRH agonists, androgens, antiandrogens and inhibitors of syntheses. Examples of estrogens include diethylstilbesterol (Stilbesterol™ and Stilphostrol™), estradiol, estrogen, esterified estrogens (Estratab™ and Menestp™) and estramustine (Emcyt™). Examples of anti-estrogens include tamoxifin (Nolvadex™) and toremifene (Fareston™). Examples of aromatase inhibitors include anastrozole (Arimidex™) and letrozol (Femara™). Examples of progestins include 17-OH-progesterone, medroxyprogesterone, and megastrol acetate (Megace™). Examples of GnRH agonists include gosereline (Zoladex™) and leuprolide (Leupron™). Examples of androgens include testosterone, methyltestosterone and fluoxmesterone (Android-F™, Halotestin™). Examples of antiandrogens include flutamide (Eulexin™), bicalutamide (Casodex™) and nilutamide (Nilandron™). Examples of inhibitors of synthesis include aminoglutethimide (Cytadren™) and ketoconazole (Nizoral™). These chemotherapeutics bind to a variety of hormones, generally estrogens and androgens or block receptors to these hormones. Cell growth and development is impaired by these chemotherapeutics by interfering with a cell's ability to bind a particular hormone, either by blocking the receptor or by binding to the hormone itself.

The antibodies class of cancer chemotherapeutics includes: rituximab (Rituxan™), trastuzumab (Herceptin™), gemtuzumab ozogamicin (Mylotarg™), tositumomab (Bexxar™) and bevacizumab. These chemotherapeutics may be antibodies that are targeted to a particular protein on the cell surface of a cancer cell. These antibodies may provide a motif for generating an immune response to the antibody and hence the cancer cell or possibly induce apoptosis. Other mechanisms of action of this class of chemotherapeutic include inhibiting stimulation from growth factors by binding to receptors on cancer cells.

The immunomodulators class of cancer chemotherapeutics includes: denileukin diftitox (Ontak™), levamisole (Ergamisol™), bacillus Calmette-Gueran, BCG (TheraCys™, TICE BCG™), interferon alpha-2a, interferon alpha-2b (Roferon-A™, Intron A™) and interleukin-2 and aldesleukin (ProLeukin™). These chemotherapeutics provide an interaction with or a stimulation of the host immune system so that the host immune system attacks the cancer cells. Interleukin-2 modulation, stimulation of cytotoxic T cells, macrophages, as well as B cells are common mechanisms of action for this class of cancer chemotherapeutics.

The angiogenesis class of cancer chemotherapeutics includes: thalidomide (Thalomid™), angiostatin and endostatin. These chemotherapeutics generally inhibit tumour vascularization thereby preventing growth of tumors by reducing blood supply to the tumours.

The rescue/protective agents class of cancer chemotherapeutics includes: dexrazoxane (Zinecard™), amifostine (Ethyol™), G-CSF (Neupogen™), GM-CSF (Leukine™), erythopoetin (Epogen™, Procrit™), oprelvekin and IL-11 (Neumega™). These chemotherapeutics work through a variety of different mechanisms of action. These mechanisms of action include protecting DNA, binding to cisplatin metabolites protecting the kidneys or cardioprotective mechanisms. Other chemotherapeutics in this class will stimulate granulocyte, macrophage, erythroid progenitor and megakaryocytic proliferation and differentiation.

Other cancer chemotherapeutics include imatinib mesylate, STI-571 (Gleevec™), 1-aspariginase (Elspar™, Kidrolase™), pegaspasgase (Oncaspar™), hydroxyurea (Hydrea™, Doxia™), leucovorin (Wellcovorin™), mitotane (Lysodren™), porfimer (Photofrin™) and tretinoin (Veasnoid™). Some chemotherapeutics may inhibit the Bcr-Abl tyrosine kinase, for example imatinib mesylate.

Prendergast et al (WO 2004/093871) describe methods for the treatment of cancer, malignancy and chronic viral infection using IDO inhibitors alone and IDO inhibitors in combination with other chemotherapeutics. Munn et al. (U.S. Patent Application publication number 2004/0234623) describe the use of inhibitors of indoleamine-2,3-dioxygenase in combination with other therapeutic modalities.

Administration of an IDO inhibitor, a chemotherapeutic, or both may be independently by systemic, parenteral, intravenous, subcutaneous, transdermal, transmucosal, intramuscular, intracranial, intraorbital, ophthalmic, intraventricular, intracapsular, intraspinal, intracisternal, intraperitoneal, intranasal, aerosol, topical, surgical, oral or parenteral administration. Dosage and duration of treatment will be determined by the practitioner in accordance with standard protocols and information concerning the activity and toxicity of the chosen compound.

Compounds or pharmaceutical compositions in accordance with this invention or for use in this invention may be administered by means of a medical device or appliance such as an implant, graft, prosthesis, stent, etc. Also, implants may be devised which are intended to contain and release such compounds or compositions. An example would be an implant made of a polymeric material adapted to release the compound over a period of time.

Example 1

IDO Inhibition Activity

The following reaction (Sono, M., Cady, S. G. Biochemistry 28, 5392-5399 (1989)) was used to measure the kinetics of inhibition of IDO using compounds of this invention as well as other compounds for comparison, as listed in Table 4.

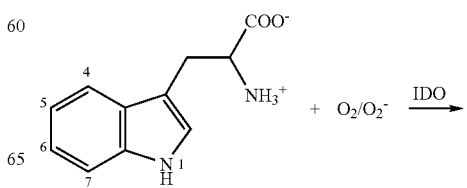

-continued

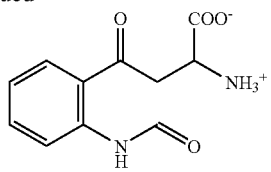

A solution of 0.1M potassium phosphate buffer (pH 6.5; optimal at 37° C.), 25 µM methylene blue, 200 µg/ml of catalase, 10 mM ascorbic acid, 50 nM of recombinant human IDO and 100 µM L-Tryptophan was prepared. The rate of product formation ($\Delta\epsilon_{321}$=3.75 mM$^{-1}$ cm$^{-1}$ for N-formylkynurenine) was determined from the slope of the initial linear absorbance increase at 321 nm as a function of time. The results for each of the compounds tested are listed in Table 4. This assay was repeated for several compounds (vitamin K$_3$ and annulin C) using differing concentrations and it was determined that the compounds inhibited IDO activity in a non-competitive manner. This feature combined with the potency of the compounds of this invention as IDO inhibitors makes them particularly useful as therapeutics.

TABLE 4

| Structure | $K_i$ | Name |
|---|---|---|
| 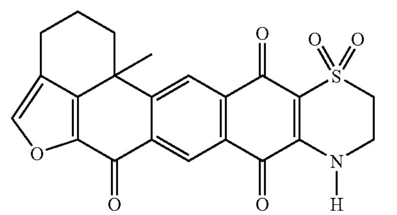 | 25 nM | Adociaquinone B |
| 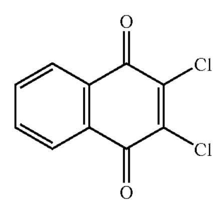 | 45 nM | Dichlone |
| 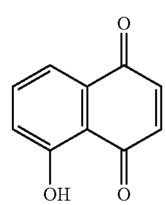 | 48 nM | Juglone |
| 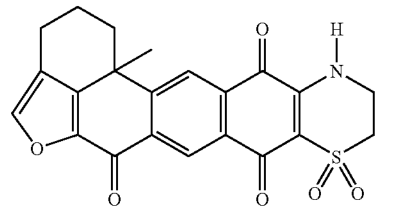 | 86 nM | Adociaquinone A |
| 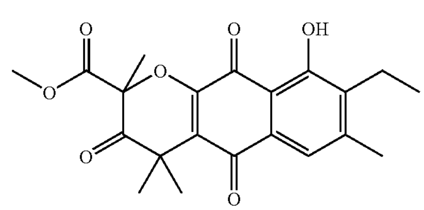 | 123 nM | Annulin B |

TABLE 4-continued

| Structure | $K_i$ | Name |
|---|---|---|
| 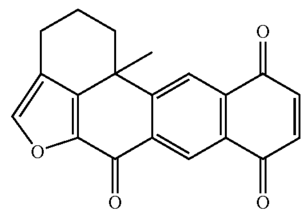 | 181 nM | Xestoquinone |
| 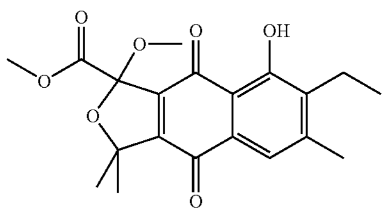 | 144 nM | Annulin C |
| 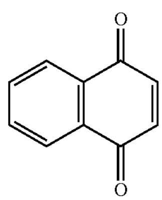 | 334 nM | 1,4 naphthoquinone |
| 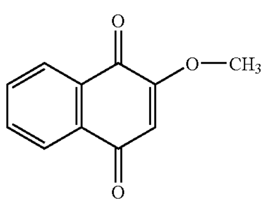 | 530 nM | |
| 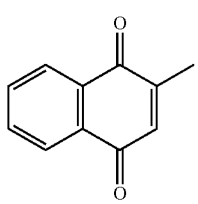 | 580 nm | Menadione (Vitamin $K_3$) |
| 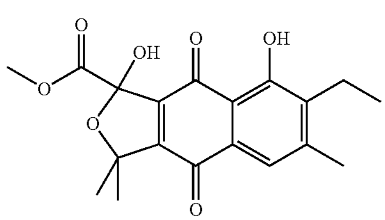 | 694 nM | Annulin A |
| | 1.18 µM | Garveatin C |

TABLE 4-continued

| Structure | $K_i$ | Name |
|---|---|---|
| 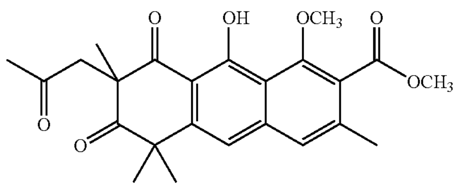 | 1.25 μM | Garvalone C |
| 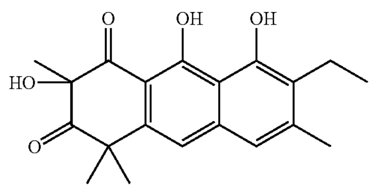 | 1.42 μM | Garveatin F |
| 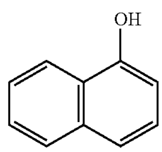 | 1.8 μM | Beta naphthol |
| 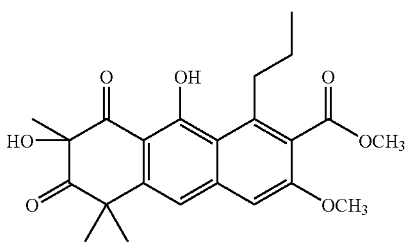 | 2.3 μM | 2-Hydroxygarvin A |
| 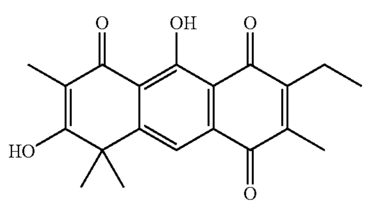 | 3.1 μM | Garveatin E |
| 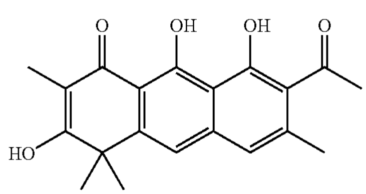 | 3.2 μM | Garveatin A |
| 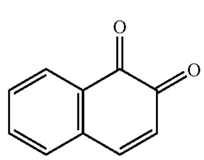 | 3.4 μM | 1,2 naphthoquinone |
| 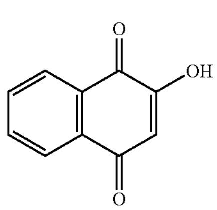 | 100 μM | |

TABLE 4-continued
| Structure | $K_i$ | Name |
|---|---|---|
| 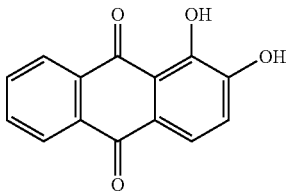 | 42 μM | Alizarin |
| 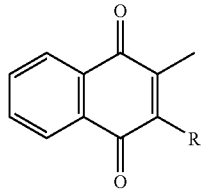 $R = CH_2CH = C(CH_3) - (CH_2CH_2CH(CH_3))_3 - CH_3$ | >40 μM | Vitamin $K_1$ |
| 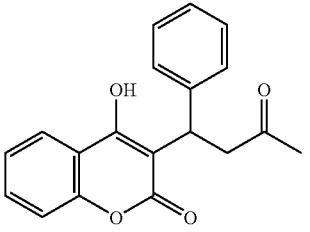 | >32 μM | Warfarin |
| 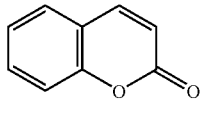 | 1.11 mM | Coumarin |
| 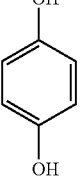 | >5 mM | Dihydroquinone |
| 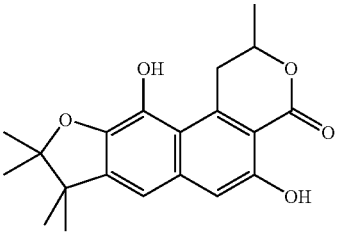 | ±2.1 mM | Garvin C |

TABLE 4-continued

| Structure | $K_i$ | Name |
|---|---|---|
| 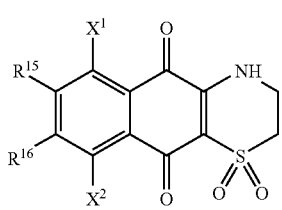 | 46 mM | Doxorubicin |

Although the foregoing invention has been described in some detail by way of illustration and example for purposes of clarity of understanding, it will be readily apparent to those of skill in the art in light of the teachings of this invention that changes and modification may be made thereto without departing from the spirit or scope of the appended claims. All patents, patent applications and publications referred to herein are hereby incorporated by reference.

We claim:

1. A compound of formula VI or a pharmaceutically acceptable salt thereof,

VI wherein, $X^1$ and $X^2$ are independently selected from: H, R, OH, OR, F, Cl, Br, I, $NH_2$, NHR, $NR_2$, CN, SH, SR, $SO_3H$, $SO_3R$, $SO_2R$, $OSO_3R$, and $NO_2$ in which R is an optionally substituted saturated or unsaturated linear, branched, or cyclic alkyl group or optionally substituted aryl group, wherein optional substituents are optionally selected from the groups consisting of aryl, ether, amino, hydroxy, ester, thioether, thiol, nitrile, nitro, amide, carbonyl, carboxyl, carboxylate, and halide groups;

$R^{15}$ and $R^{16}$ are individual substituents independently selected from: H, OH, OR, and a linear, branched, or cyclic, saturated or unsaturated alkyl group in which one or more carbon atoms of the alkyl group are optionally and independently substituted or are replaced by an oxygen (O) or sulfur (S) atom or a secondary amino (NR) group, where R is as defined above;

or $R^{15}$ and $R^{16}$ are fused and form a substituted or unsubstituted, aromatic or non-aromatic, mono-, bi-, or tricyclic ring system containing C, O, N or S atoms;

excluding a compound having the structure:

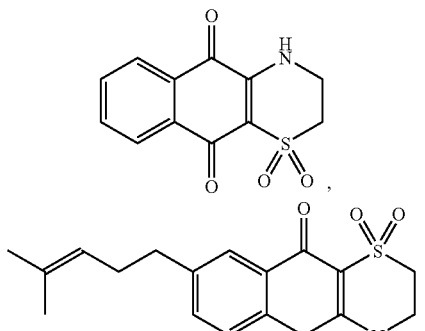

Conicaquinone A

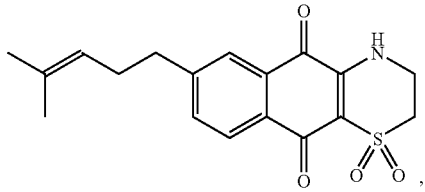

Conicaquinone B

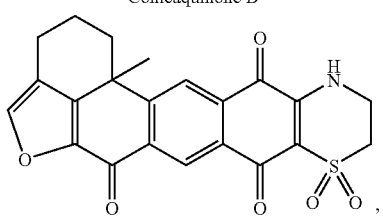

Adociaquinone A

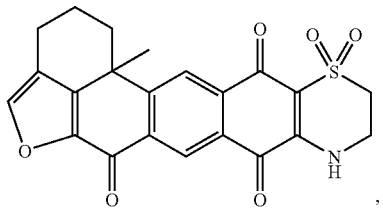

Adociaquinone B

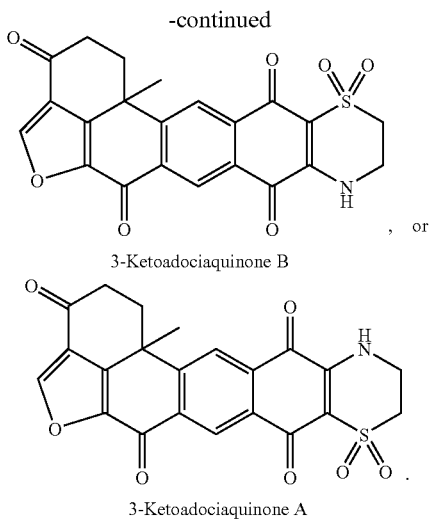

3-Ketoadociaquinone B, or

3-Ketoadociaquinone A

2. The compound or salt of claim 1, wherein if R is alkyl, it is optionally substituted with a substituent selected from the groups consisting of: aryl, ether, amino, hydroxy, ester, thioether, thiol, nitrile, nitro, amide, carbonyl, carboxyl, carboxylate and halide.

3. The compound or salt of claim 1, wherein if R is aryl or is substituted by aryl, the aryl is optionally substituted with a substituent selected from the group consisting of: ether, amino, hydroxy, ester, thioether, amide, nitro, carbonyl, carboxyl, carboxylate and halide.

4. The compound or salt of claim 1, wherein $R^{15}$ and $R^{16}$ are individual substituents and one or both of $R^{15}$ and $R^{16}$ is an alkyl group as defined, in which at least one carbon atom is optionally substituted with a substituent selected from the group consisting of: aryl, ether, amino, hydroxy, ester, thioether, thiol, nitrile, nitro, amide, carbonyl, carboxyl, carboxylate and halide.

5. The compound or salt of claim 1, wherein $R^{15}$ and $R^{16}$ are individual substituents, independently selected from the group consisting of: H, $C_1$-$C_6$ alkyl, OH, COOH, C(O)R, COOR and halogen, with R as defined.

6. The compound or salt of claim 1, wherein $R^{15}$ and $R^{16}$ are individual substituents independently selected from the group consisting of: H, OH, $C_1$-$C_3$ alkyl and $C_1$-$C_3$ alkoxy.

7. The compound or salt of claim 1, wherein $R^{15}$ and $R^{16}$ are fused and form a structure selected from the group consisting of:

(f)
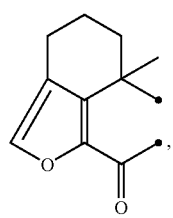

(g)
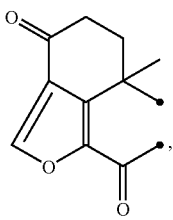

(h)
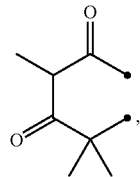

(i)
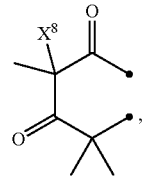

(j)
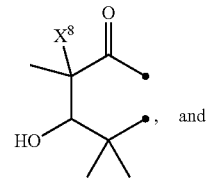

(k)
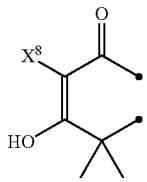

wherein $X^8$ has the definition of $X^1$ and $X^2$.

8. The compound of or salt of claim 1 having the structure

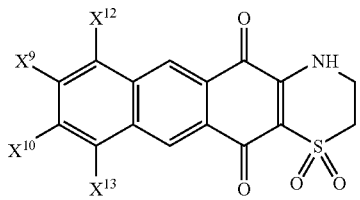

VII wherein each of $X^9$, $X^{10}$, $X^{12}$ and $X^{13}$ individually have the definition of $X^1$ and $X^2$.

9. The compound or salt of claim 8, wherein $X^1$, $X^2$, $X^8$, $X^9$, $X^{10}$, $X^{12}$ and $X^{13}$ when present are independently selected from the group consisting of: H, $C_1$-$C_6$ alkyl, OH, COOH, C(OR), COOR and halogen, with R as defined.

10. The compound or salt of claim 8, wherein $X^1$, $X^2$, $X^8$, $X^9$, $X^{10}$, $X^{12}$ and $X^{13}$ when present are independently selected from the group consisting of: H, OH, $C_1$-$C_3$ alkyl and $C_1$-$C_3$ alkoxy.

11. A compound or a tautomeric form of a compound as shown in Table 3, or a pharmaceutically acceptable salt thereof.

12. A composition comprising a compound or salt of claim 1, and a pharmaceutically acceptable carrier.

* * * * *